United States Patent [19]
Croft et al.

[11] Patent Number: 5,680,418
[45] Date of Patent: Oct. 21, 1997

[54] REMOVING LOW FREQUENCY INTERFERENCE IN A DIGITAL FM RECEIVER

[75] Inventors: Thomas M. Croft; Torbjörn W. Sölve, both of Cary, N.C.; Paul W. Dent, Stehag, Sweden

[73] Assignee: Ericsson, Inc., Research Triangle Park, N.C.

[21] Appl. No.: 345,848

[22] Filed: Nov. 28, 1994

[51] Int. Cl.⁶ .......................... H03D 13/00; H04L 22/06
[52] U.S. Cl. .................... 375/346; 375/254; 375/340; 375/350; 455/309; 329/341; 371/5.1; 371/37.7
[58] Field of Search .................................. 329/300, 341, 329/343; 455/304, 306, 307, 309; 375/285, 340, 346, 350, 229, 254, 344, 348, 371; 395/185.01; 371/5.1, 48, 67.1, 30, 37.7

[56] References Cited

U.S. PATENT DOCUMENTS

| | | |
|---|---|---|
| 3,593,150 | 7/1971 | Michishita et al. |
| 4,380,082 | 4/1983 | Namiki ........................ 375/102 |
| 4,501,004 | 2/1985 | Yoshida et al. |
| 4,575,862 | 3/1986 | Tahara et al. |
| 4,803,701 | 2/1989 | Rhodes. |
| 4,908,581 | 3/1990 | Honjo. |
| 4,995,104 | 2/1991 | Gitlin ........................... 370/6 |
| 5,283,815 | 2/1994 | Chennakeshu et al. |
| 5,339,456 | 8/1994 | Dickerson. |

FOREIGN PATENT DOCUMENTS

| | | |
|---|---|---|
| 2122376 | 9/1972 | France. |
| WO91/14329 | 9/1991 | WIPO. |
| WO94/26024 | 11/1994 | WIPO. |

*Primary Examiner*—Melvin Marcelo
*Assistant Examiner*—Jean B. Corrielus
*Attorney, Agent, or Firm*—Burns, Doane, Swecker & Mathis, L.L.P.

[57] ABSTRACT

In a digital FM receiver having a demodulator that receives a radio signal and generates therefrom a phase sample whose behavior determines an output of the demodulator, an apparatus for removing a low-frequency interference signal from the phase sample converts the phase sample into a frequency sample which is then high-pass filtered to produce a filtered frequency sample. The filtered frequency sample is then converted into a filtered phase sample, which may be further demodulated in accordance with known techniques. Converting the phase sample into a frequency sample may be performed by a first order difference circuit. Converting the filtered frequency sample into the filtered phase sample may be performed by an integrator. Because the demodulator may produce degraded performance when the inventive apparatus is applied to a radio signal that does not have low-frequency interference, in another aspect of the invention the demodulator is further provided with a circuit for detecting the presence of the low-frequency interference signal in the radio signal, and alternatively selecting, in response thereto, either the filtered or original phase sample to be supplied to further demodulation circuitry.

16 Claims, 7 Drawing Sheets

REMOVING LOW FREQUENCY INTERFERENCE IN A DIGITAL FM RECEIVER

BACKGROUND

The present invention relates to techniques for removing low frequency interference from a received angle modulated signal carrying digital information, and more particularly to techniques for removing this interference from phase samples of the received angle modulated signal.

Techniques for communicating digital information by using it to modulate a carrier signal are well known. A modulator-demodulator (modem) is a well-known device designed for this purpose. In response to the increasing demand for mobile capability, modems have been designed with interfaces for communicating the information over a wireless medium, such as cellular telephone technology.

In this regard, it is known to use Manchester coding (also known as split-phase coding) of binary data in the transmission of data. An example of one such system that utilizes this technique is the Advanced Mobile Phone Service (AMPS) system in North America. Manchester coding is first applied by representing each information bit as a two-bit codeword, or symbol: a "1" bit is represented by the symbol "10", and a "0" bit is represented by the symbol "01". The encoded digital information is then impressed upon the radio carrier frequency by means of frequency modulation (FM).

A number of techniques for demodulating a Manchester-coded digital FM signal are known. A preferred technique is disclosed in U.S. Pat. No. 5,475,705 by Paul W. Dent, entitled "Demodulator For Manchester-Coded FM Signals", filed Apr. 29, 1993, which is expressly incorporated herein by reference. One of the characteristics of this preferred technique is the fact that, instead of applying the received radio signal to a frequency discriminator, as in the earlier prior art, demodulation is instead based on the behavior of the phase or complex vector value of the received signal. The polarities of the information bits may be determined by measuring the phase excursions in the middles of the Manchester symbols. A phase reference is established from a plurality of candidate phase references as a basis for comparison of the mid-symbol phase. The phase can be measured at the start-points and end-points of the symbols and averaged, or measured a plurality of times during each symbol period to generate a reference phase.

Important to the proper functioning of a wide-band data modem that uses the preferred demodulation technique is the ability to receive a signal that is substantially free from interference. Unfortunately, when the signal is received from a wireless medium, interference can arise from a variety of sources. In particular, it has been found that a particular type of cellular telephone system base station that is currently in use introduces a large, slowly varying residual FM component that can cause serious problems to a wide-band data modem. This residual FM component has been found to be sinusoidal with a frequency of 36 Hz and a maximum frequency deviation of about 1 KHz, although these parameters may vary with time. When the received Manchester-coded signal is demodulated, this residual FM impairment causes a frequency (and therefore phase) error that varies more rapidly and by a larger amount than the demodulator's phase averaging circuit (which includes a frequency error estimator) can handle. As a result, approximately 50 per cent of the blank-and-burst messages may be lost, which of course is unacceptable.

SUMMARY

It is therefore an object of the present invention to provide a technique for removing low frequency interference in a digital FM receiver that employs a demodulation technique based on the behavior of the phase or complex vector value of the received signal.

It is a further object of the present invention to additionally provide a technique for detecting the presence of low frequency interference in a received digital FM signal.

In accordance with one aspect of the present invention, the foregoing and other objects are achieved by an apparatus in a digital FM receiver having a demodulator that receives a radio signal and generates therefrom a phase sample whose behavior determines an output of the demodulator, the apparatus being for removing a low-frequency interference signal from the phase sample. The apparatus converts the phase sample into a frequency sample which is then high-pass filtered to produce a filtered frequency sample. The filtered frequency sample is then converted into a filtered phase sample, which may be further demodulated in accordance with known techniques. Converting the phase sample into a frequency sample may be performed by a first order difference circuit. Converting the filtered frequency sample into the filtered phase sample may be performed by an integrator.

Because the demodulator may produce degraded performance when the inventive apparatus is applied to a radio signal that does not have low-frequency interference, in another aspect of the invention the demodulator is further provided with a circuit for detecting the presence of the low-frequency interference signal in the radio signal, and alternatively selecting, in response thereto, either the filtered or original phase sample to be supplied to further demodulation circuitry.

In accordance with one embodiment, this detection is performed by low-pass filtering the frequency sample and measuring the energy in the band where the low-frequency impairment would appear, if present. This measured energy value is then compared to a threshold value. If the measured energy exceeds the threshold value, then the low-frequency interference signal is present.

Alternatively, this detection may be performed by including, within the demodulator, a memory for storing a table of base station system identification values (IDs) of those base stations known to generate the low-frequency noise. The detection of signal impairment is then performed by comparing a received system ID with those contained in the table. A match indicates the presence of the low-frequency interference.

In another alternative embodiment, the apparatus for removing a low-frequency interference signal from the phase sample is provided in a demodulator to produce a corrected demodulated signal. The demodulator is further provided with means for demodulating the radio signal without the benefit of the inventive apparatus, thereby producing a non-corrected demodulated signal. Each of the corrected and non-corrected demodulated signals is checked for error content (for example by performing a cyclic redundancy check on each one), and an output from the demodulator is selected from the corrected and non-corrected demodulated signals on the basis of their respective error contents.

BRIEF DESCRIPTION OF THE DRAWINGS

The objects and advantages of the invention will be understood by reading the following detailed description in conjunction with the drawings in which.

DETAILED DESCRIPTION

The various features of the invention will now be described with respect to the figures, in which like parts are identified with the same reference characters.

A first embodiment of the inventive low frequency interference suppressor 100 will now be described with respect to the block diagram shown in FIG. 1(a). The low frequency interference suppressor 100 has an input for receiving phase samples 101 that are preferably produced by a demodulator for Manchester-coded FM signals (not shown) in accordance with the techniques described in U.S. Pat. No. 5,475,705 which has been incorporated herein by reference. It is assumed that the phase samples 101 are impaired by the presence of the above-described unwanted low frequency interference.

The phase samples 101 are converted into frequency samples 105 by a first order difference circuit 103, which determines the difference between successive samples. That is, each of the frequency samples 105 represents frequency change per sample. The frequency samples 105 are reduced modulo $2\pi$, and then supplied to a low-pass filter 107 which filters at a rate of 80 Ksamples/sec in order to allow for oversampling of the 10 Kbits/sec Manchester-coded, data by a factor of eight. The low-pass filter 107 is preferably a second-order Butterworth filter mapped to the digital domain via a bilinear transformation. The corner frequency of this filter, whose purpose is to pass only the impairment, is 150 Hz. The output of the low-pass filter 107 is supplied to an integrator 113, which generates modulo $2\pi$ values of the estimated phase impairment 115. Integration is done at the rate of 80 KHz, allowing the estimated phase impairment 115 to be at the correct sample rate for subtraction from time aligned copies of the original phase samples 101 in subtractor 117. (Time alignment is necessary to compensate for the delays associated with generating the estimated phase impairment.) To accomplish this, the output of the integrator 113 is supplied to a subtrahend input of the subtractor 117. The other (positive) input of the subtractor 117 receives the output from a delay line 153, which time aligns the original phase samples 101 with the estimated phase impairment 115. The output of the subtractor 117, after being reduced modulo $2\pi$, is the corrected phase signal 119, which is supplied back to the demodulator for Manchester-coded FM signals to complete the demodulation process.

Figure 1A:
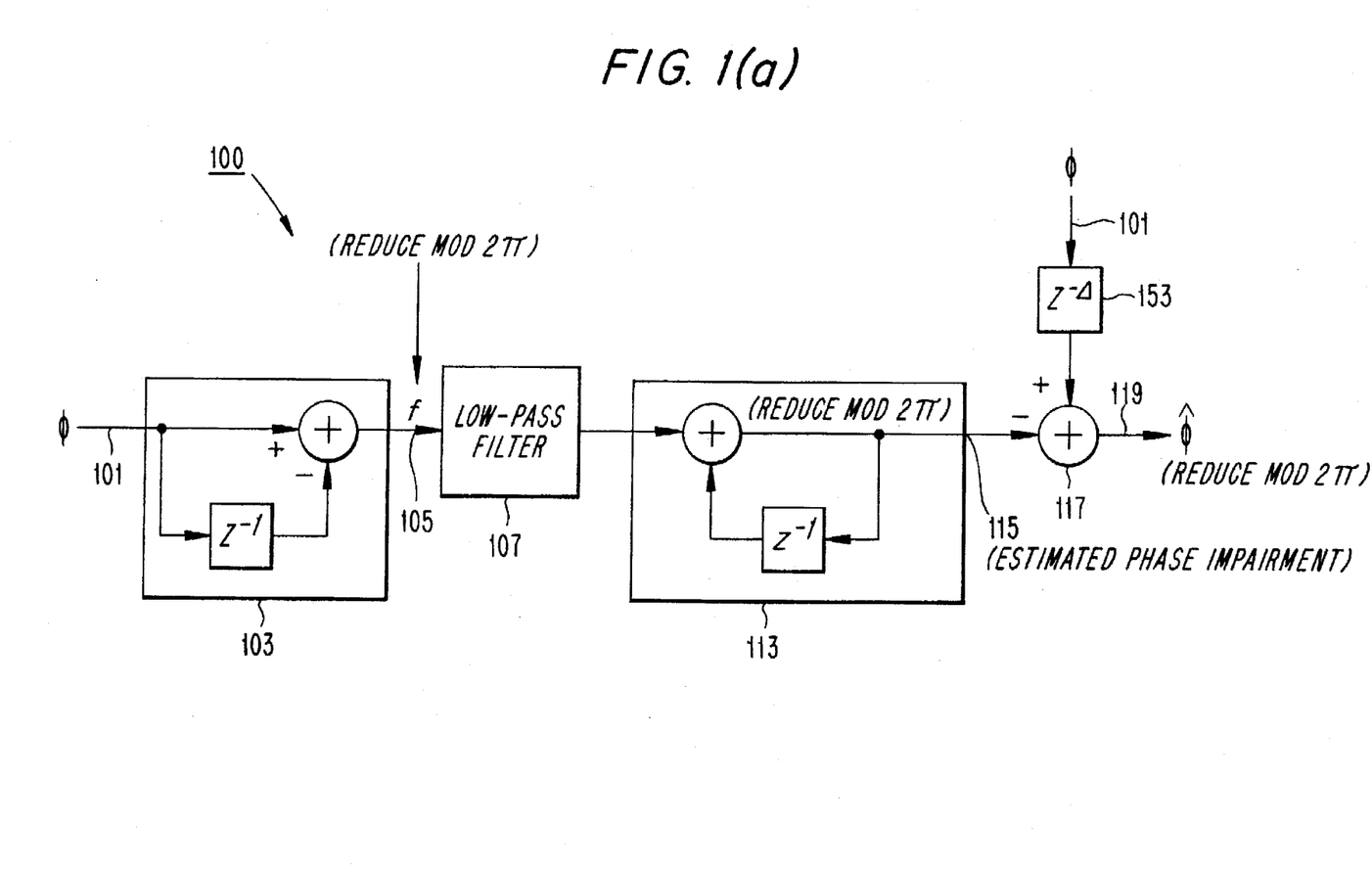
FIGS. 1(a) and 1(b) show illustrative embodiments of a low frequency interference remover in accordance with one aspect of the invention.
Figure 1B:
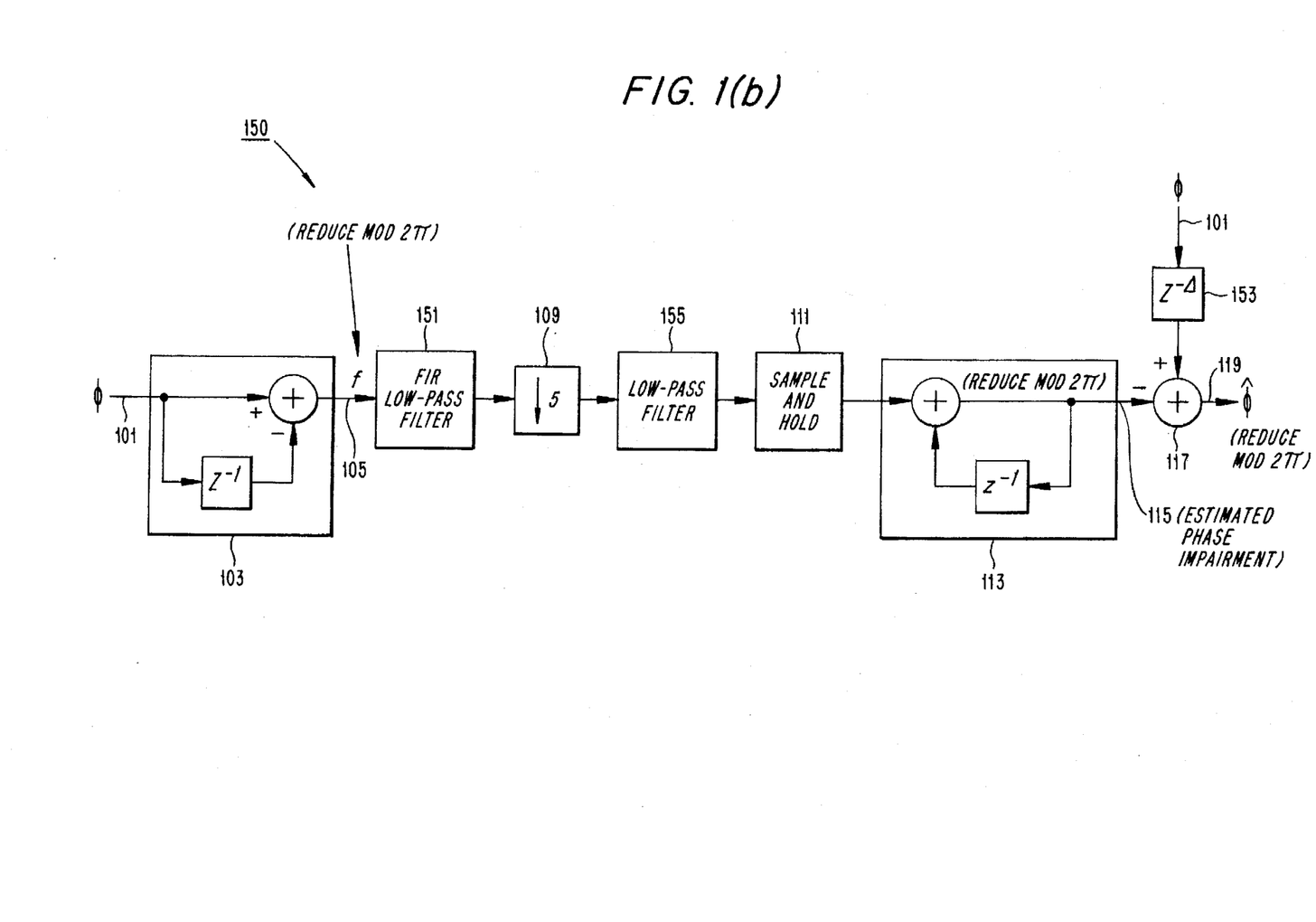

The circuit depicted in FIG. 1(a) is useful for explaining the theory of operation of this aspect of the invention, but is not preferred because of the higher processing requirements imposed by the need to perform a second-order low-pass filtering operation at an 80 KHz sample rate. A less processing-intensive circuit that operates in accordance with the theory described above with respect to FIG. 1(a) is illustrated in FIG. 1(b). Here, the low frequency interference suppressor 150 includes many of the same components described above with respect to FIG. 1(a). One difference, however, is that the low-pass filter 155 (equivalent to the low-pass filter 107 shown in FIG. 1(a)) operates on frequency samples that are being supplied at a 16 KHz rate rather than at 80 KHz. In practice, such samples may be readily available. However, for purposes of testing this arrangement, such samples may readily be generated by supplying 80 KHz frequency samples 105 from the first order difference circuit 103 to an anti-aliasing finite impulse response (FIR) low-pass filter 151 which will allow sample rate reduction by the decimation filter 109. For this purpose, the FIR low-pass filter 151 is preferably a linear-phase 7-tap filter with a 3-dB cutoff frequency of 6 KHz. The low-pass filter 155 then operates on the 16 KHz output samples of the decimation filter 109. The low-pass filter 155 has the same frequency response as the low-pass filter 107 described above with respect to FIG. 1(a), but has to be scaled in the bilinear transformation for the lower sample rate of 16 KHz. The 16 KHz output of the low-pass filter 155 is then supplied to a sample and hold circuit 111 which repeats each of the 16 KHz samples five times to generate an 80 KHz supply of filtered samples that are supplied to the integrator 113. As described above with respect to FIG. 1(a), the integrator 113 generates modulo $2\pi$ values of the estimated phase impairment 115 which are subtracted from time aligned copies of the original phase samples 101.

The above-described scheme for removing low-frequency interference in a digital FM receiver suffers from several drawbacks. First, it is sensitive to the delay of the low-pass filter 155. For example, in a test of this type of system, it was necessary to adjust the delay line 153 to delay the original phase signals 101 by 122 samples in order to achieve time alignment with the estimated phase impairment 115. Also, since the low-pass filter 155 was of the infinite impulse response (IIR) variety, it was impossible to provide a linear phase (constant group delay) response. Therefore, the noise passed by this filter undergoes a phase change and cannot, in general, cancel that in the original phase waveform, even if the two signals are time aligned.

An alternative embodiment of an inventive low frequency interference suppressor 200 will now be described with respect to FIG. 2. This alternative embodiment is preferred because it avoids the problems of time delay and distortion of the phase of the noise by converting the phase samples 101 to frequency samples 105, directly removing the undesired residual FM component, and then converting the corrected frequency samples into corrected phase samples which are then demodulated in accordance with the preferred technique.

Thus, as with the previously described embodiments, the low frequency interference suppressor 200 has an input for receiving phase samples 101 that are preferably produced by a demodulator for Manchester-coded FM signals (not shown) in accordance with the techniques described in U.S. Pat. No. 5,475,705, which has been incorporated herein by reference. It is again assumed that the phase samples 101 are impaired by the presence of the above-described unwanted low frequency interference.

The phase samples 101 are converted into frequency samples 105 by a first order difference circuit 103, which determines the difference between successive samples. The frequency samples 105 are reduced modulo $2\pi$, and then supplied to a high-pass filter 201 which filters at a rate of 80 Ksamples/sec. In order to reduce processing requirements, the high-pass filter 201 is preferably a first-order Butterworth filter in the high-pass configuration. Of course, a second- or third-order filter could also be used instead, but this would impose higher processing requirements on the low frequency interference suppressor 200. The Butterworth filter is preferred because it exhibits a flat response in the pass band. However, this type of filter is not a requirement; any type of high-pass filter could be used instead. It has been empirically determined that a corner (i.e., 3-dB) frequency of approximately 750 Hz works best for a first-order filter in this application. A higher corner frequency harms the wide-band data too much, and a lower corner frequency inadequately attenuates the impairment.

The filtered frequency samples 203 are then supplied to an integrator 113 whose output, after reduction by modulo $2\pi$, is the sequence of corrected phase samples 205.

Figure 2:
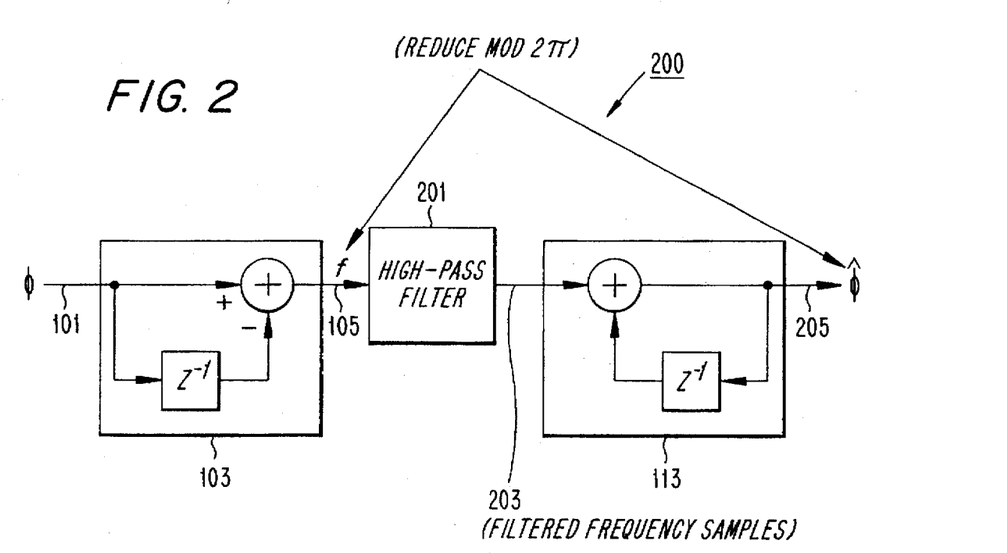
FIG. 2 is a block diagram of an alternative, preferred embodiment of an inventive low frequency interference remover in accordance with the present invention.

Despite the simplicity of the preferred embodiment illustrated in FIG. 2, this arrangement operates entirely at the 80 KHz sample rate of the incoming phase samples 101, and therefore places more demands on the processing hardware that is utilized to implement the various components.

The performance of each of the above-described embodiments was assessed by means of simulation. First, without applying any correction whatsoever, the performance of a demodulator for Manchester-coded FM signals was simulated for a received signal with and without the impairment in a static gaussian channel. These baseline numbers showed that, in the case of no impairment, demodulation of data could be performed more or less perfectly beginning at an $E_b/N_o$ below 10 dB, where $E_b$ is defined as (signal power$_{average}$)/(bit rate), and $N_o$ is defined as (noise power$_{average}$)/(noise bandwidth). When the impairing noise is added to the received signal, however, each message out of one hundred frames was lost for every value of $E_b/N_o$ up to and including 31 dB.

Use of an early version (absent the delay line 153) of the low frequency interference suppressor 100 (depicted in FIG. 1(a)) was able to bring the lost message rate down considerably at high values of $E_b/N_o$, but still produced a loss of 91 per cent of the frames at 10 dB in a static gaussian channel. Some of this performance appeared to be attributable to a misalignment between the phase samples 101 and the estimated phase impairment 115 that are presented to the subtractor 117. For this reason, the delay line 153 was introduced in an attempt to time align the original phase samples 101 with the estimated phase impairment 115. This helped performance considerably, yielding a lost message rate of 22 per cent at 10 dB $E_b/N_o$.

The embodiment of FIG. 1(b) was also simulated to determine how it would affect the performance of a demodulator for Manchester-coded FM signals. After optimizing the amount of delay produced by the delay line 153, it was found that the lost message rate above 10 dB $E_b/N_o$ in a static gaussian channel could be brought back to zero, but at 10 dB the system suffered a lost frame rate of 99 per cent.

Figure 3:
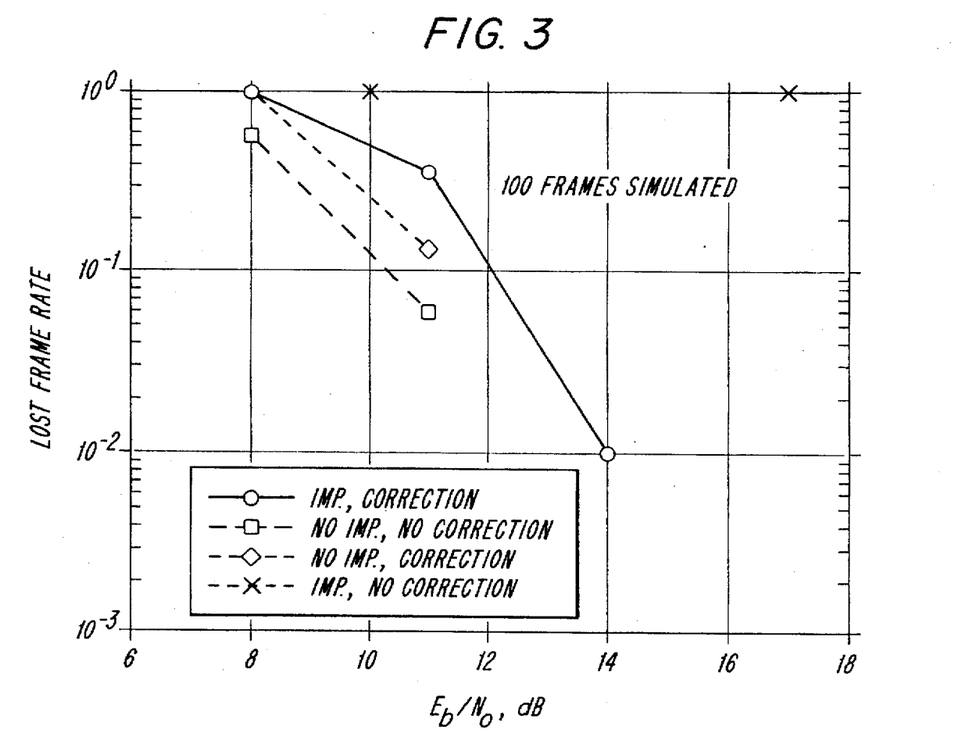
FIG. 3 is a graph of test results for a demodulator utilizing the preferred embodiment of the inventive low frequency interference remover operated in flat fading with a vehicle speed of 100 km/hr.

A similar static gaussian simulation was performed for the preferred embodiment of the low frequency interference suppressor 200 shown in FIG. 2. It was found that this configuration brought the lost message rate at 10 dB $E_b/N_o$ down to 8 per cent. The test results for this embodiment in flat fading with a vehicle speed of 100 km/hr are summarized in the graphs depicted in FIG. 3. It can be seen that although the preferred technique is capable of restoring performance to an acceptable level of lost messages when the received signal is impaired by noise, a price is paid for high-pass filtering a portion of the wide-band data when no impairment is present. That is, when no impairment is present, some worsening in performance occurs relative to a system with no correction whatsoever.

Figure 4:
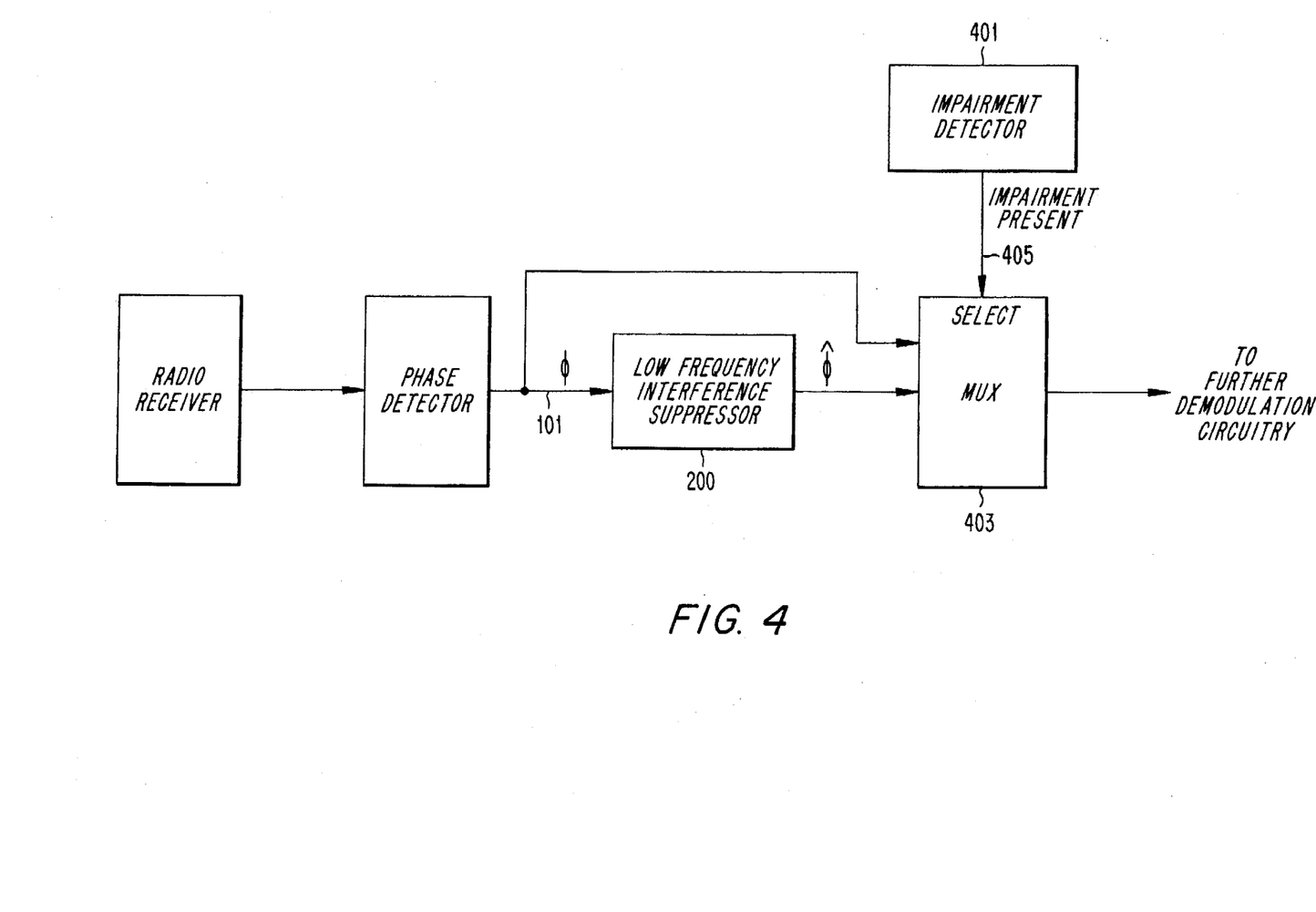
FIG. 4 is a block diagram of a demodulator that utilizes the inventive low frequency interference remover, and which further includes circuitry that is capable of detecting the presence or absence of impairment, in accordance with another aspect of the invention.

In accordance with another aspect of the invention, the drawback introduced by high-pass filtering of an unimpaired received signal is greatly reduced. Referring now to FIG. 4, this is accomplished by deploying the low frequency interference suppressor 200 in a system that is further capable of detecting the presence or absence of impairment. When the impairment detector 401 determines that the received signal has been impaired by the introduction of noise, its output (impairment present 405) controls the multiplexor (MUX) 403 to select the output of the low frequency interference suppressor 200. The output of the MUX 403 is then supplied to further demodulation circuitry (not shown) which operates in accordance with known techniques. If no impairment is detected, however, then the impairment detector 401 causes the MUX 403 to select the original phase samples 101, thereby avoiding the degraded performance that would otherwise be introduced by use of the low frequency interference suppressor 200.

Figure 5:
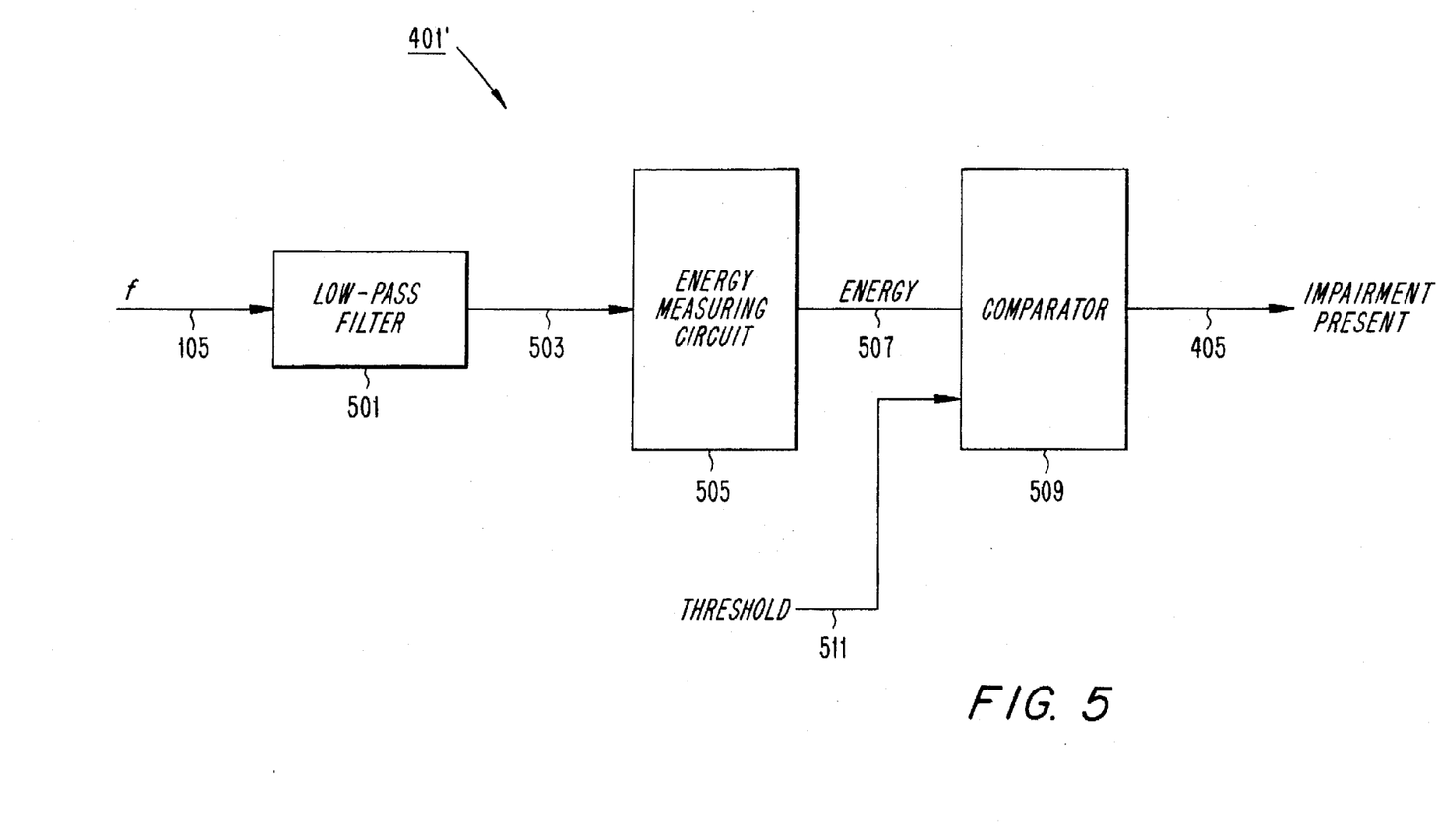
FIG. 5 is a block diagram of one embodiment of the impairment detector in accordance with the invention.

One embodiment of the impairment detector 401 will now be described with respect to FIG. 5. In this embodiment, the impairment detector 401' receives, as an input, the frequency samples 105 that are produced by the first order difference circuit 103 (see FIG. 2). A low-pass filter 501 filters the frequency samples 105 to allow only those frequency components to pass that are in the band where the low-frequency impairment would appear. The filtered frequency samples 503 are then supplied to an energy measuring circuit 505 which measures the strength of these signals, preferably by determining the sum of squared samples. This energy measurement 507 is supplied to one input of a comparator 509, so that it can be compared with a threshold value 511. When the energy measurement 507 exceeds the threshold value 511, the comparator generates the impairment present signal 405, which is supplied to the MUX 403 as shown in FIG. 4. To determine an appropriate threshold value, the energy in the impairment band may be measured with and without the impairment present for a large number of channel conditions. Then, histograms of the energy distributions may be plotted for the two cases. A threshold value that differentiates between the two cases may then be identified and selected.

Figure 6:
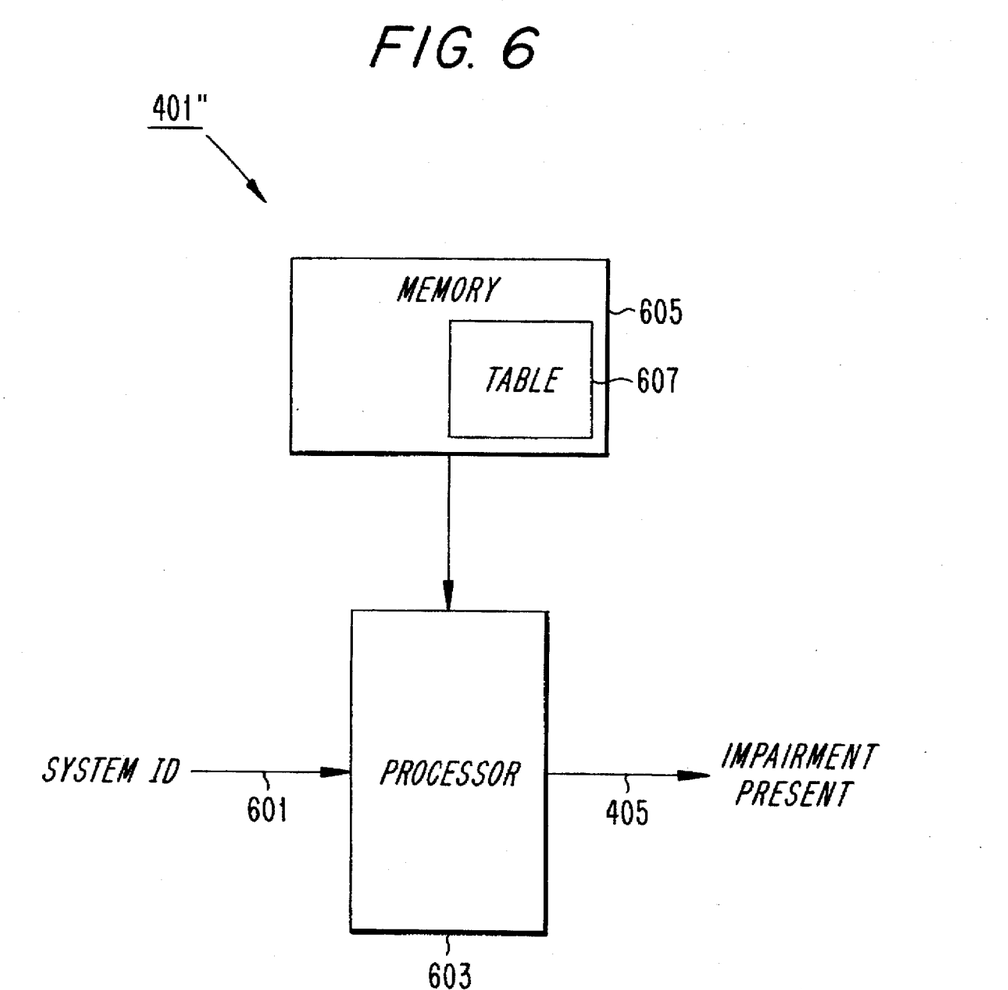
FIG. 6 is a block diagram of an alternative embodiment of the impairment detector in accordance with the present invention.

An alternative embodiment of the impairment detector 401 will now be described with respect to FIG. 6. In this embodiment, the impairment detector 401" receives, as an input, the system identification (ID) 601 of the base station (not shown) with which the receiver equipment is communicating. This information is typically provided by a base station to the mobile station that it is serving so that the mobile station will know what cell it is in. A processor 603 compares the system ID 601 with a table of IDs 607 that are stored in a memory 605, which is preferably a read-only memory (ROM). The table of IDs 607 is generated by collecting the system IDs of all cells that are known to contain the particular type of base station equipment that generates the unwanted low-frequency noise.

If the processor 603 determines that the system ID 601 matches any one of the IDs stored in the table 607, then it asserts the impairment present signal 405. It is noted that, while this solution is good in theory, it may not always produce reliable results because cellular telephone system operators occasionally move base station equipment from one cell site to another. As a result, the table 607 may not always represent the most up-to-date allocation of base station hardware. However, in a geographical region where the type of base station equipment being used in any given cell is stable, this embodiment offers a practical solution.

Figure 7:
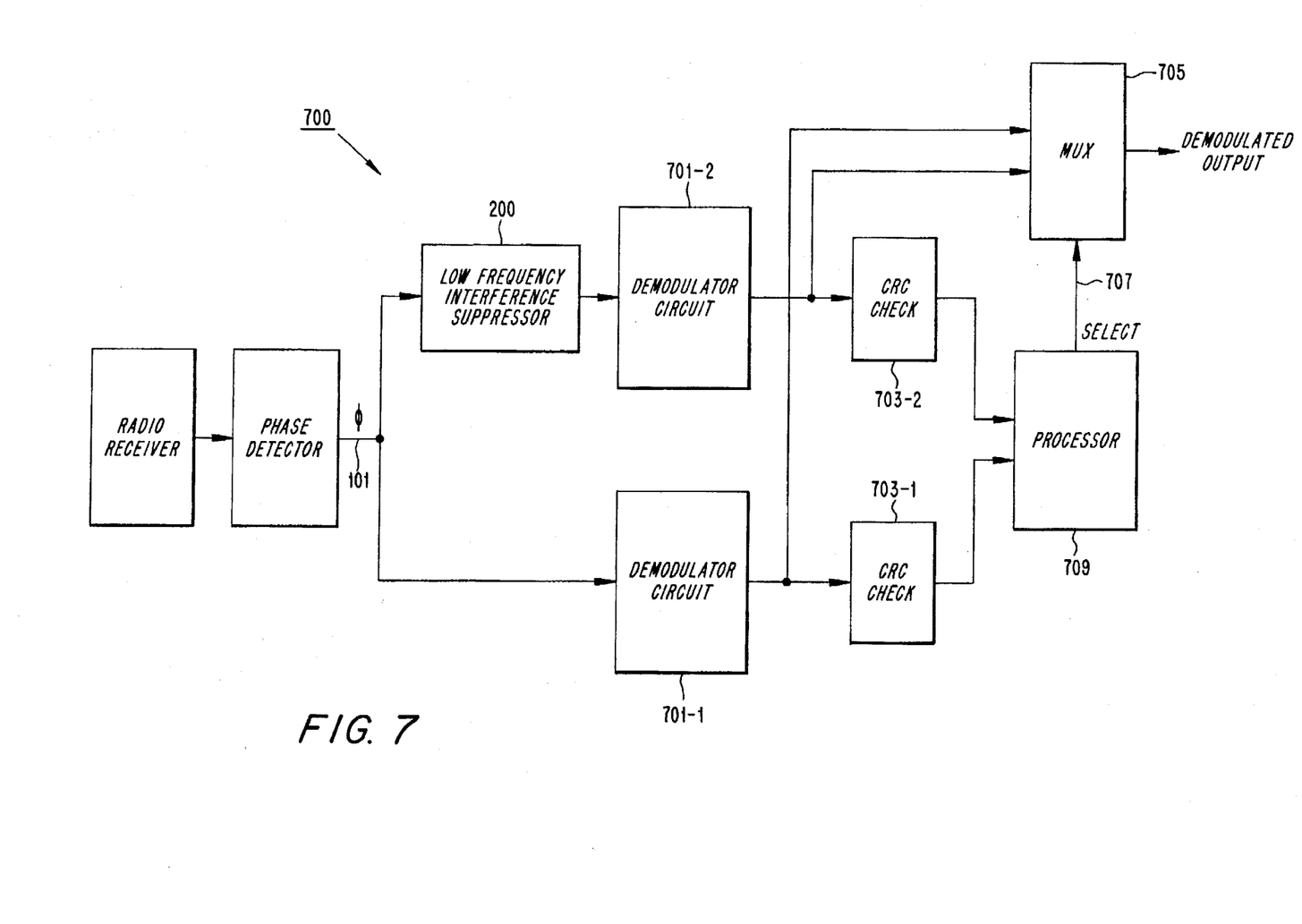
FIG. 7 is a block diagram of a demodulator that incorporates another method for reducing the performance degradation associated with high-pass filtering an unimpaired received signal, in accordance with another aspect of the present invention.

Another method for reducing the performance degradation associated with high-pass filtering an unimpaired received signal is illustrated in FIG. 7. Here, phase samples 101 are produced as described above. These are supplied to each of two parallel processing paths. In one path, the phase samples 101 are supplied directly to a first demodulator circuit 701-1. In the other path, the phase samples 101 are supplied to the low frequency interference suppressor 200, whose output is supplied to a second demodulator circuit 701-2 that is functionally identical to the first demodulator circuit 701-1. The outputs from each of the first and second demodulator circuits 701-1, 701-2 are then supplied to respective ones of two cyclic redundancy check (CRC) circuits 703-1, 703-2, as well as to respective first and second inputs of a MUX 705. The outputs from the two CRC circuits 703-1, 703-2 are supplied to a processor 709 which determines the identity of the path that is producing the most error-free results. A select signal 707 is generated by the processor 709 which causes the MUX 705 to pass the most error-free signal as the demodulated output 709 from the demodulator 700.

While this last approach is not the most economical or efficient of the above-described solutions, it is nonetheless viable.

The invention has been described with reference to a particular embodiment. However, it will be readily apparent to those skilled in the art that it is possible to embody the invention in specific forms other than those of the preferred embodiment described above. This may be done without departing from the spirit of the invention. The preferred embodiment is merely illustrative and should not be considered restrictive in any way. The scope of the invention is given by the appended claims, rather than the preceding description, and all variations and equivalents which fall within the range of the claims are intended to be embraced therein.

What is claimed is:

1. In a digital FM receiver having a demodulator that receives a radio signal and generates therefrom a phase sample whose behavior determines an output of the demodulator, an apparatus for removing a low-frequency interference signal from the phase sample, comprising:

input means for receiving the phase sample;

first means for converting the phase sample into a frequency sample;

high-pass filter means for removing, from the frequency sample, energy associated with frequencies below a predetermined frequency, the high-pass filter means supplying a filtered frequency sample at a filter output; and second means for converting the filtered frequency sample into a filtered phase sample.

2. The apparatus of claim 1, wherein the first means is a first order difference circuit.

3. The apparatus of claim 1, wherein the second means is an integrator.

4. In a digital FM receiver, a demodulator apparatus comprising:

input means for receiving a radio signal;

means for converting the radio signal into a phase sample;

means for removing a low-frequency interference signal from the phase sample, comprising:

first means for converting the phase sample into a frequency sample;

high-pass filter means for removing, from the frequency sample, energy associated with frequencies below a predetermined frequency, the high-pass filter means supplying a filtered frequency sample at a filter output; and second means for converting the filtered frequency sample into a filtered phase sample;

detection means for detecting the presence of the low-frequency interference signal in the radio signal;

selection means, operatively coupled to the detection means, for alternatively selecting, as an output from the selection means, the phase sample when the low-frequency interference signal is not detected in the radio signal, or the filtered phase sample when the low-frequency interference signal is detected in the radio signal; and demodulation means for generating a demodulated signal on the basis of the output from the selection means.

5. The demodulator apparatus of claim 4, wherein the detection means comprises:

input means for receiving the frequency sample;

low-pass filter means for removing, from the frequency sample, energy associated with frequencies above a second predetermined frequency, the low-pass filter means supplying a second filtered frequency sample at a low-pass filter output;

means for measuring an energy value of the second filtered frequency sample; and means for comparing the energy value of the second filtered frequency sample with a predetermined energy value, and generating an indication of the presence of the low-frequency interference signal in the radio signal when the energy value of the second filtered frequency sample exceeds the predetermined energy value.

6. The demodulator apparatus of claim 4, wherein the detection means comprises:

input means for receiving a system identification value associated with a base station that transmitted the radio signal;

table means for storing one or more predetermined system identification values;

means for determining whether the received system identification value matches any of the one or more predetermined system identification values stored in the table means, and if a match is found then indicating the presence of the low-frequency interference signal in the radio signal.

7. In a digital FM receiver, a demodulator apparatus comprising:

input means for receiving a radio signal;

means for converting the radio signal into an original phase sample;

means for removing a low-frequency interference signal from the original phase sample, comprising:

first means for converting the original phase sample into a frequency sample;

high-pass filter means for removing, from the frequency sample, energy associated with frequencies below a predetermined frequency, the high-pass filter means supplying a filtered frequency sample at a filter output; and second means for converting the filtered frequency sample into a filtered phase sample;

first demodulation means for generating a corrected demodulated signal from the filtered phase sample;

second demodulation means for generating a non-corrected demodulated signal from the original phase sample;

first error detection means for detecting a first quantity of errors contained in the corrected demodulated signal;

second error detection means for detecting a second quantity of errors contained in the non-corrected demodulated signal;

selection means, operatively coupled to the first and second demodulation means and to the first and second error detection means, for alternatively selecting, as an output from the selection means, either the corrected demodulated signal or the non-corrected demodulated signal on the basis of a comparison of the first quantity of errors with the second quantity of errors.

8. The demodulator apparatus of claim 7, wherein the selection means comprises:

means for alternatively selecting the corrected demodulated signal when the first quantity of errors is less than the second quantity of errors, or the non-corrected demodulated signal when the first quantity of errors is not less than the second quantity of errors.

9. In a digital FM receiver having a demodulator that receives a radio signal and generates therefrom a phase sample whose behavior determines an output of the demodulator, a method of removing a low-frequency interference signal from the phase sample, comprising the steps of:

receiving the phase sample;

converting the phase sample into a frequency sample;

removing, from the frequency sample, energy associated with frequencies below a predetermined frequency to produce a filtered frequency sample; and converting the filtered frequency sample into a filtered phase sample.

10. The method of claim 9, wherein the step of converting the phase sample into a frequency sample comprises generating a difference between the phase sample and a previous phase sample.

11. The apparatus of claim 9, wherein the step of converting the filtered frequency sample into a filtered phase sample comprises the step of integrating the filtered frequency sample.

12. In a digital FM receiver, a method of demodulating a radio signal, comprising the steps of:

receiving the radio signal;

converting the radio signal into a phase sample;

performing a procedure to remove a low-frequency interference signal from the phase sample, the procedure comprising the steps of:

converting the phase sample into a frequency sample;
removing, from the frequency sample, energy associated with frequencies below a predetermined frequency to produce a filtered frequency sample; and
converting the filtered frequency sample into a filtered phase sample;

detecting the presence of the low-frequency interference signal in the radio signal;

alternatively selecting, for use as a selected phase sample, the phase sample when the low-frequency interference signal is not detected in the radio signal, or the filtered phase sample when the low-frequency interference signal is detected in the radio signal; and generating a demodulated signal on the basis of the selected phase sample.

13. The method of claim 12, wherein the step of detecting the presence of the low-frequency interference signal in the radio signal comprises the steps of:

removing, from the frequency sample, energy associated with frequencies above a second predetermined frequency to produce a second filtered frequency sample;

measuring an energy value of the second filtered frequency sample; and comparing the energy value of the second filtered frequency sample with a predetermined energy value, and generating an indication of the presence of the low-frequency interference signal in the radio signal when the energy value of the second filtered frequency sample exceeds the predetermined energy value.

14. The method of claim 12, wherein the step of detecting the presence of the low-frequency interference signal in the radio signal comprises the steps of:

receiving a system identification value associated with a base station that transmitted the radio signal;

determining whether the received system identification value matches at least one predetermined system identification value stored in a table, and if a match is found then indicating the presence of the low-frequency interference signal in the radio signal.

15. In a digital FM receiver, a method of demodulating a radio signal, comprising the steps of:

receiving the radio signal;

converting the radio signal into an original phase sample;

performing a procedure for removing a low-frequency interference signal from the original phase sample, the procedure comprising the steps of:

converting the original phase sample into a frequency sample;
removing, from the frequency sample, energy associated with frequencies below a predetermined frequency to produce a filtered frequency sample; and
converting the filtered frequency sample into a filtered phase sample;

generating a corrected demodulated signal from the filtered phase sample;

generating a non-corrected demodulated signal from the original phase sample;

detecting a first quantity of errors contained in the corrected demodulated signal;

detecting a second quantity of errors contained in the non-corrected demodulated signal;

alternatively selecting either the corrected demodulated signal or the non-corrected demodulated signal on the basis of a comparison of the first quantity of errors with the second quantity of errors.

16. The method of claim 15, wherein the step of alternatively selecting comprises the step of alternatively selecting the corrected demodulated signal when the first quantity of errors is less than the second quantity of errors, or the non-corrected demodulated signal when the first quantity of errors is not less than the second quantity of errors.

* * * * *